United States Patent [19]

Erlich

[11] Patent Number: 4,943,284
[45] Date of Patent: Jul. 24, 1990

[54] SHEATH FOR DEVICES FOR INJECTING OR WITHDRAWING BODY FLUIDS

[76] Inventor: Frederick L. Erlich, 29540 Meadowlane Dr., Southfield, Mich. 48076

[21] Appl. No.: 240,268

[22] Filed: Sep. 6, 1988

Related U.S. Application Data

[63] Continuation of Ser. No. 23,813, Mar. 9, 1987, Pat. No. 4,772,275.

[51] Int. Cl.⁵ .............................................. A61M 5/00
[52] U.S. Cl. .................................. 604/263; 604/192; 604/198; 206/365
[58] Field of Search ............... 604/171, 172, 280≧284; 128/4, 6–9, 11, 23, 763–768; 206/361–365, 438

[56] References Cited

U.S. PATENT DOCUMENTS

| | | | |
|---|---|---|---|
| 2,847,995 | 8/1958 | Adams | 604/198 |
| 3,886,930 | 6/1975 | Ryan | 128/763 |
| 3,902,500 | 9/1975 | Dryden | 604/171 |
| 4,168,699 | 9/1979 | Hauser | 128/768 |
| 4,596,554 | 6/1986 | Dastgeer | 604/101 X |
| 4,664,653 | 2/1986 | Sagstetter | 604/198 |
| 4,725,267 | 2/1988 | Vaillancourt | 604/198 |
| 4,778,453 | 10/1988 | Lopez | 604/198 X |
| 4,795,432 | 1/1989 | Karczmer | 604/263 X |

*Primary Examiner*—Dalton L. Truluck
*Attorney, Agent, or Firm*—Arnold S. Weintraub; Gerald R. Black

[57] ABSTRACT

A device for sterile disposal of a device used to withdraw or inject fluids from or into the body comprising a tubular sheath disposed in a rolled-up fashion around the body fluid device proximate one end thereof. The length of the sheath is great enough to permit the sheath, when unrolled, to extend beyond the end of the body fluid device and for a sufficient distance to permit ready enclosure thereof and subsequent sealing off of the contents of the sheath. A method for using the device is also disclosed. The device is particularly useful in combination with a catheter of conventional design.

8 Claims, 2 Drawing Sheets

SHEATH FOR DEVICES FOR INJECTING OR WITHDRAWING BODY FLUIDS

This is a continuation of the application Ser. No. 023,813, filed Mar. 9, 1987 now U.S. Pat. No. 4,772,275 issued Sept. 20, 1988.

BACKGROUND OF THE INVENTION

1. Field of the Invention

This invention relates to the field of sterile disposal of devices such as catheters, and the like used for injecting or withdrawing fluid into or from the body and, in particular, to a sheath disposed around such a device which may be drawn up to enclose the used device and tied off for sterile disposal thereof.

2. Description of the Prior Art

Catheters and other devices for use in draining of accumulated fluids from body cavities or injecting fluids into the body have been widely used in many medical fields for a long period of time. With reference to catheters, there are numerous types of designs, any of which are particularly adapted to be inserted into a particular body cavity. For example, a urethral catheter is designed to drain urine from the bladder. A ventricular catheter is adapted to drain excess cerebrospinal fluid from the brain. A peritoneal catheter is used to drain fluid from the periotoneum; as kidney dialysis. An enema catheter is used to introduce fluid into the gastrointestinal track.

All of the above-mentioned types of catheters, as well as others too numerous to enumerate, have certain design features in common. A typical medicinal catheter is formed of hollow, flexible tubing. The tubing is typically comprised of a silicone elastomer such as silicone rubber, a substance which is soft and non-irritating to body tissues. A typical catheter will have a body contact end and a non-body contact end. One or more inlets will be formed adjacent the body contact end. An outlet will be formed adjacent the non-body contact end, and frequently will be comprised of the non-body contact end itself. Catheters designed for different purposes may additionally comprise other structures, but the ones enumerated are generally common to all catheters. Also, the dimensions of the catheter may vary greatly and will be adapted to the purpose for which it is intended. For example, a catheter adapted as a urinary catheter may typically have an outside diameter in the range of 0.3–0.8 millimeters. In contrast, a ventricular catheter will have a much smaller diameter.

No matter the particular type, most catheters are used in a similar manner. One end of the catheter is inserted into the body cavity containing the fluid which needs to be drained. The catheter may be inserted directly through a body orifice, such as is the usual case with urethral catheters, or a special opening may have to be made. For example, an opening may have to be made into a vein and the catheter threaded through the vein until it reaches the appropriate body cavity, such as is the case with ventricular catheters. After the catheter is inserted, some means of collecting the fluid must be attached to the non-body contact end. Sometimes, as for ventricular catheters, the catheter will remain within the body and the excess fluid drained will be absorbed by another area of the body. More commonly, however, the excess fluid will simply be collected in a bag or bottle and discarded. The catheter may be left in place for long periods of time, or the excess body fluid may be drained wuickly and the catheter removed after only a short period of insertion.

Irrespective of what type of catheter is used, how long it remains in place, or what type of body fluid it is used to drain, all catheters must eventually be disposed of. When the catheter is no longer needed, it will be removed from the body and then be disposed. If the catheter has been used with a patient suffering from a communicable or infectious disease, the catheter so used will be highly likely to be contaminated with an infectious agent. If such contaminated catheters are simply discarded in a casual manner, the possibility of contaminating attendant personnel and perhaps other patients is high.

The same disposal problems arises with other medical devices that come in contact with body fluids. For example, syringes are commonly used to inject or withdraw fluids from, for example, the circulatory system, the lymphatic system, the cerebrospinal system, etc. Most commonly, the syringes are disposable and used only once. Since they must be disposed of after use, the possibility of contamination from a used syringe is quite significant.

The problem of disposal of contaminated catheters and other devices is particularly acute in the management of patients afflicted with such highly infectious diseases as acquired immune deficiency syndrome (AIDS). For diseases such as AIDS, where the exact mechanism of transmission is poorly understood, it is extremely important that attending personnel be isolated as much as possible from all potential sources of infection. Even more significantly, the apprehension by persons attending AIDS patients that they may be contaminated with the disease by the mere handling of objects used in the treatment of the patients, such as used catheters or syringes, may interfere with the ability of the attending personnel to provide proper care and treatment of the patient.

Heretofore, the only solution to the problem of sanitary disposal of catheters and other devices used in the treatment of highly infectious patients have been ad hoc, unsatisfactory ones. For example, a used catheter may be removed from the patient and immediately place within a sterile container, such as a plastic bag, the container then being sealed. However, due to the shape of the catheter and the flexible, resilient material from which it is typically made, it is difficult to place the unwieldly catheter within the container without having to attempt to fold it or roll it up. Obviously, the motions involved in doing this cause much unnecessary and dangerous handling of the contaminated catheter.

It would be desirable to provide a means for sterile containment and subsequent disposal of a device such as a catheter which has been in contact with body fluids which minimizes handling of the contaminated object.

It would also be desirable to provide a means of disposal which could easily enclose and contain the used device by a simple, one-step unrolling motion.

It would also be highly desirable to provide a device mounted disposal means which is easy to use and has the additional advantages of being economical to manufacture and sterilize.

SUMMARY OF THE INVENTION

The device and method disclosed and claimed herein provides for easy and effective containment of a medical device such as a catheter, syringe, cannula, drainage tube etc., which has been in contact with body fluids which is simple and inexpensive to manufacture, and may be easily disposed of. The invention provides a device for sterile disposal of devices used for injecting fluid into the body or withdrawing fluid from a body cavity, the device comprising a sheath formed of a thin, flexible, fluid imprevious material which is disposed around the device in a rolled-up fashion. The sheath may be either permanently attached to the device by adhesive or sonic welding or may be snap fit thereon. The length of the sheath is such that, when it is unrolled, it will enclose the contaminated portion of the device and may be sealed off for sterile containment of the contents. With reference to an embodiment particularly suited for disposal of a catheter, the device comprises in combination; a hollow, tubular catheter having at least one inlet disposed proximate a non-body contact end; and a tubular catheter sheath disposed around the catheter medial of a body contact end thereof. The length of the catheter sheath is great enough to permit it to extend beyond the body contact end of the catheter for a sufficient distance such that the body contact end may be enclosed by the sheath, with a sufficient additional length to permit ready sealing off of the contents of the sheath. The catheter sheath is disposed around the catheter in a rolled-up fashion.

To use the sheath of the instant invention, the contaminated device is first removed from the patient. The rolled-up sheath is simply unrolled to its full length. After it is unrolled, it will extend beyond the contaminated end of the used device. The end of the sheath may be then sealed to completely contain the inlet and the contaminated portion of the device therein. The device encased in the sheath may be then simply discarded. Alternatively, the sheath may be unrolled as the device is being withdrawn.

In some cases it will be desirable to also enclose the non-body contact end of the device. This is particularly true of catheters. In most cases, the outside of the non-body contact end of the catheter will not normally be contaminated. Additionally, it is also possible that the outside of the non-body contact end of any type of catheter may become contaminated through malfunction, improper use, splashing, etc. Therefore, to provide sterile disposal of virtually the entire length of the catheter, one embodiment of the instant invention provides a second, sheath disposed adjacent the first sheath and medial of the non-body contact end of the catheter. The second sheath has a length sufficiently along to enclose completely the non-body contact end of the catheter and permit subsequent sealing off of the contents of the non-body contact end of the apparatus. In order to use this embodiment, the second sheath is unrolled to enclose the non-body contact end and sealed as described above. Subsequently, the first sheath is unrolled to contain and enclose the body contact end of the catheter. Its end is then sealed off in the same manner. In a similar manner, the dual sheaths could be used to completely enclose any device contaminated along most of its length with body fluids.

In order to isolate the infectious material contained within the sheaths, it is highly desirable that they be formed of a material which is both flexible and impervious. The material should be impervious to body fluid, vapors formed thereof, atmospheric air, gases, and micro-organisms. The material must also be flexible enough to permit ready rolling up of the sheath during manufacture. Additionally, the material must be one that can be either fabricated in a sterile manner orone which can withstand sterilization after manufacture. Typical examples of such a material include: polyethylene; high density polyethylene; polypropyl; polytetrafluoroethlyne; polyvinyldene fluoride; polyvinylchorlride; polyethylene teraphathalate; silicone elastomers; other synthetic organic polymers; and the like. For a device such as a syringe, where there may be a possibility of puncture of the sheath by the device, the material should also be resistant to tearing and puncture.

BRIEF DESCRIPTION OF THE DRAWING

The various features, advantages and other uses of this invention will become more apparent by referring to the following detailed description and drawing in which.

DESCRIPTION OF THE PREFERRED EMBODIMENTS

Figure 1:
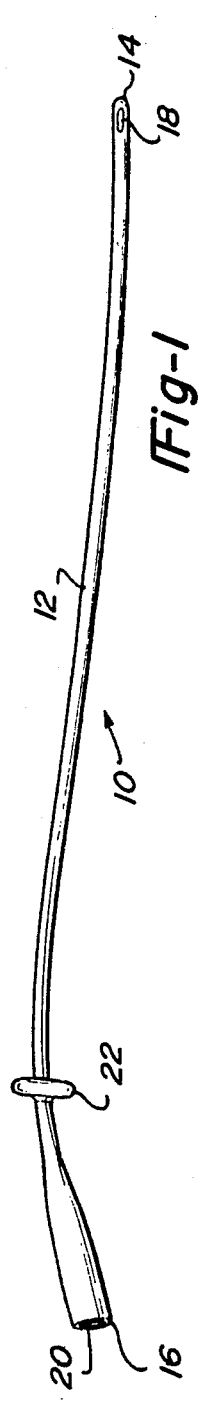
FIG. 1 is a perspective view of a device fabricated in accordance with the teachings of the instant invention showing a catheter sheath in a rolled-up position disposed around a typical catheter.

Throughout the following description and drawing, identical reference numerals are used to refer to the same components shown in multile figures of the drawing.

Referring now to the drawing, and to FIG. 1 in particular, there is shown a device 10 for sterile disposal of an apparatus 12 for use in a body cavity. While the embodiments shown in the drawing are particularly adapted to catheters and syringes, it is to be understood that this is for illustrative purposes and that the instant invention is applicable to any device that comes in contact with body fluids. The apparatus 12 is hollow and tubular, and has a body contact end 14 and a non-body contact end 16. At least one outlet 18 is formed in the wall of the tubular apparatus 12 adjacent the body contact end 14 thereof. An outlet 20 is formed adjacent the non-body contact end 16 of the apparatus 12, and, as shown in FIG. 1, the outlet 20 may be formed by the non-body contact end 16.

Disposed around and attached to the apparatus 12 is a first sheath 22. The first sheath is disposed around the apparatus 12 medial the body contact and non-body contact ends thereof. A typical placement of first sheath 22 is depicted in FIG. 1, where first sheath 22 is shown disposed around apparatus 12 in near proximity to outlet 20. By disposing apparatus 12, the first sheath 22, when unrolled, will enclose and contain most of the length of apparatus 12. The first sheath 22 is attached to the apparatus 12 by a suitable means such as sonic welding, a suitable adhesive or bonding agent, etc. Alternately, the first sheath 22 may be attached to the apparatus 12 by a snap fit.

Figure 2:
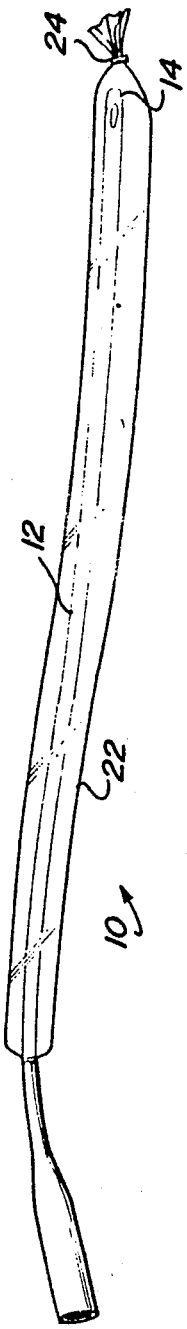
FIG. 2 illustrates the device of FIG. 1 with the catheter sheath having been unrolled and sealed off.

As depicted in FIG. 1, first sheath 22 is shown rolled up around apparatus 12. FIG. 2 depicts first sheath 22 after it has been unrolled for its entire length. It will be seen from an examination of FIG. 2 that the length of first sheath 22 is long enough such that it will extend beyond the body contact end 14 of apparatus 12. The extension of first sheath 22 beyond the body contact end 14 will permit the sealing off thereof to enclose the contents of first sheath 22. Means of sealing 24 is provided to seal off the end of first sheath 22 to completely enclosed the contents thereof. Means of sealing 24 may be in a conventional type of sealing means, such as a paper coated wire twist tie, a rubber band, adhesive tape, a slip, a spring clip, etc. Alternatively, the end of sheath 22 may be provided with a self-sealing means such as a lip and groove formed therein.

The method of use of the device 10 for sterile disposal of a used device, e.g., a catheter will now be described. First, it is desirable that device 10 be made sterile prior to use. The device 10 may be either manufactured in a manner such that it is sterile or that it may be sterilized after manufacture by any conventional method. Prior to use, the first sheath 22 will be in the rolled up position shown in FIG. 1.

The catheter is used in the conventional manner by inserting the body contact end 14 with the inlet 18 formed therein into a body cavity (not shown). The outlet 20 of the apparatus 12 will be attaced to a means (not shown) for storing the unwanted fluids. In certain cases, outlet 20 may be first connected with an auxiliary tube (not shown) which is in turn connected to the storage means.

After the body fluid has been drained, the catheter will be removed from the body cavity by removing body contact end 14 carrying inlet 18 therefrom. The outlet 20 disposed on non-body contact end 16 will be then detached from the storage means and/or auxiliary tube. The first sheath 22 will then be unrolled by grasping it and pulling it toward body contact end 14. After it is fully unrolled and extends beyond the body contact end 14 of the apparatus 12, it will be sealed off by applying sealing means 24. FIG. 2 illustrates the range of the device of the instant invention after the steps of unrolling and sealing off have been performed. It may be seen from an examination of FIG. 2 that the contaminated portions of the apparatus 12, including particularly inlet 18, are fully contained within the sealed off first sheath 22. Since the catheter was in use, the surface exposed during the unrolling procedure will not have been exposed to the contaminated body fluids. Thus, the impervious area provided by the unrolled and sealed off first sheath 22 will effectively prevent cross-contamination between the used catheter and any other object, such as other hospital equipment or another patient or attendant.

Alternately, the first sheath 22 may be unrolled as the apparatus 12 is being wthdrawn from the body. It is then sealed of as described above. This alternate method provides even stronger protection against the possibility of contamination.

Figure 3:
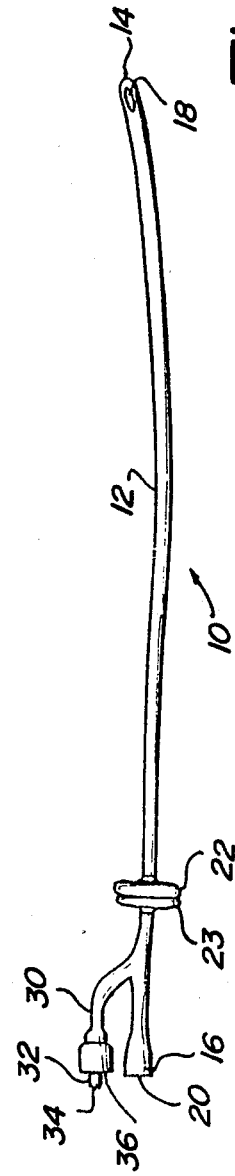
FIG. 3 is a perspective view of an alternative embodiment of the device of the present invention in which a secondary sheath is provided.
Figure 4:
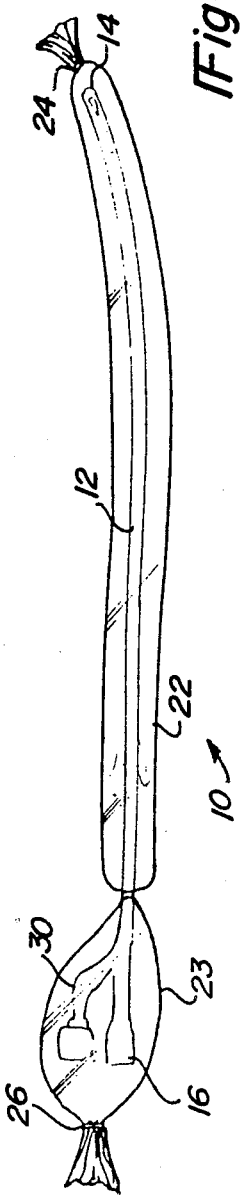
FIG. 4 illustrates the device of FIG. 3 with both sheaths unrolled and sealed off.

Another embodiment of the device of the instant invention is illustrated in FIGS. 3 and 4. The apparatus 12 shown in FIG. 3 has the additional structure of a branch 30 formed near the non-body contact end 16 of the apparatus 12. The branch 30 is hollow and tubular and is in fluid communication with apparatus 12. A hollow, rigid member 32 is shown partially inserted into the end of branch 30. Disposed within hollow, rigid insert 32 is a plug 34 comprised of softer material, typically silicone rubber. A rubber band 36 is shown disposed on the outside of branch 30 to hold rigid insert 32 and plug 34 in correct position. The purpose of the additional structures shown is so that the needle of a syringe (not shown) may be inserted into apparatus 12 by plunging it into plug 34. By means of the syringe, several additional functions may be added to the functioning of the catheter. For example, if additional suction is needed to withdraw the body fluids from the cavity, the suction may be supplied by means of a syringe. Conversely, medication may be inserted into the body cavity be means of the syringe.

In FIGS. 3 and 4, a second sheath 23 is provided. FIG. 3 illustrates the second sheath 23 in its rolled-up position. Second sheath 23 is disposed immediately adjacent first sheath 22 and medially of the non-body contact end 16 of apparatus 12. As with first sheath 22, the length of second sheath 23 is such that, when second sheath 23 is fully unrolled, a portion thereof will extend beyond the non-body contact end 16 of apparatus 12. Second sheath 23, upon being unrolled, may then be sealed off with sealing means 26 in a manner analogous to sheath 22.

FIG. 4 depicts the device of FIG. 3 with both sheaths 22, 23 unrolled and sealed off. It may be seen from an examination of FIG. 4 that virtually the entire length of apparatus 12 is encased by sheaths 22, 23 thereby preventing contamination from virtually any part of apparatus 12 from reaching the environment outside the sheaths 22, 23. Sterile containment of the entire apparatus 12 may be necessary in cases where both ends 14, 16 thereof are likely to become contaminated.

Figure 5:
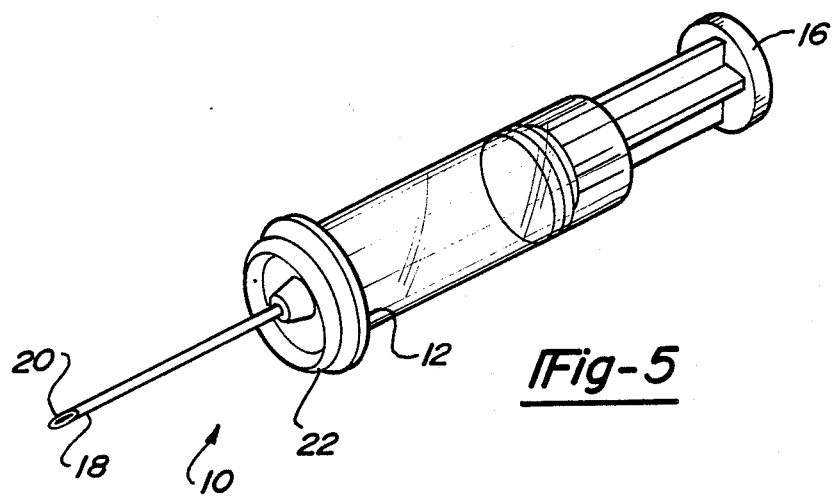
FIG. 5 is a perspective view of a syringe with a sheath disposed in a stowed-retracted position.
Figure 6:
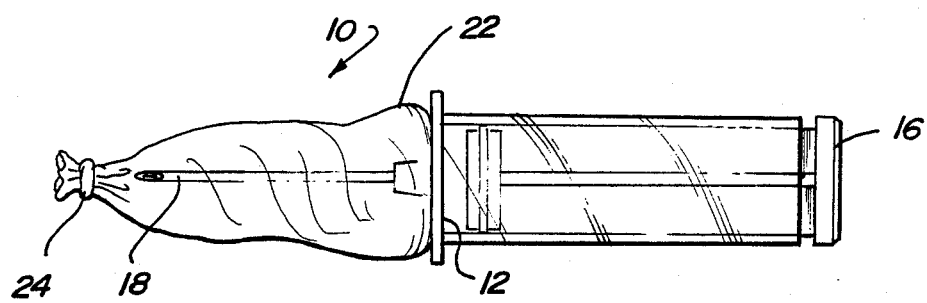
FIG. 6 is the syringe of FIG. 5 with the sheath being extended and sealed off.

Another embodiment of the device 10 is depicted in FIGS. 5 and 6, where the apparatus 12 is a conventional syringe with the sheath 22 in a stowed-retracted position, and in an extended position, respectively.

In summary, there has been disclosed a sheath for sterile containment and disposal of a device used to inject or withdraw fluid into or from the body. The device comprises a tubular sheath disposed in slowed-retracted fashion around the device and in close proximity to an end thereof. The length of the sheath, when extended, is great enough to permit the sheath to extend beyond the end of the device for a sufficient distance such that the end of the sheath may be sealed, thereby providing complete and sanitary containment of the contents thereof.

While the device and method of the present invention has been described with regard to certain embodinments and exemplifications thereof, they are not intended to be so limited but solely by the claims appended hereto.

I claim:

1. A disposable medical device for use in a patient, the device protecting attendant personnel from contamination associated with the device after the device has been withdrawn from the patient, the device comprising:
   (a) a hollow tubular apparatus having a body contact end and a non-body contact end, the apparatus having a tip disposed at the body contact end; and
   (b) a flexible sheath being secured to the hollow tubular apparatus between the body contact end and the non-body contact end, the flexible sheath having a stowed-retracted position and an enveloping position, the flexible sheath being completely stowed when in the stowed-retracted position, the flexible sheath being unstowed and extended in the enveloping position, the length of the flexible sheath in the enveloping position being great enough to extend beyond the tip of the hollow tubular apparatus; and wherein the flexible sheath is in the stowed-retracted position until after the body-contact end of the hollow tubular apparatus is removed from the circulatory system of the patient, at which time the flexible sheath is extended beyond the tip of the hollow tubular apparatus.

2. A disposable medical device for use in a patient, the device protecting attendant personnel from contamination associated with the device after the device has been withdrawn from the patient, the device comprising:
  (a) body-circuit means for delivering medicinal fluids into the circulatory system of the patient, the body-conduit means having a body contact end and a non-body contact end, the body-contact end being rigid, the body-conduit means having a passageway that enables fluids to be transmitted therethrough to the circulatory system of the patient, the body-conduit means having a tip disposed at the body-contact end; and
  (b) flexible means for containing the body-conduit means, the flexible means being secured to the body-conduit means between the body contact end and the non-body contact end, the flexible means being made of a material that is resistant to tearing and puncture, the flexible means having a stowed-retracted position and an enveloping position, the flexible means being compactly stowed when in the stowed retracted position, the flexible means being unstowed and extended in the enveloping position, the flexible means being in the stowed-retracted position when the body-conduit means is in the enveloping position being great enough to extend beyond the tip of the body-conduit means, the flexible means being in the stowed-retracted position until the body-conduit means is withdrawn from circulatory system of the patient, at which time the body-conduit means is extended into the enveloping position.

3. A disposable medical device for use in a patient, the device protecting attendant personnel from contamination associated with the device after the device has been withdrawn from the patient, the device conprising:
  (a) a hollow rigid tubular apparatus having a passageway that enables medicinal fluids to be transmitted therethrough from and to the circulatory system of the patient, the hollow rigid tubular apparatus having a body contact end and a non-body contact end, the body-contact end being rigid, the hollow rigid tubular apparatus having a tip disposed at the body contact end; and
  (b) a flexible sheath being secured to the hollow tubular apparatus between the body contact end and the non-body contact end, the flexible sheath having a stowed-retracted position and an enveloping position, the flexible sheath being compactly stowed when in the stowed-retracted position, the flexible sheath being unstowed and extended in the enveloping position, the sheath being in the stowed-retracted position when the hollow tubular apparatus is in the body of the patient, the length of the flexible sheath in the enveloping position being great enough to extend beyond the tip of the hollow rigid tubular apparatus.

4. A method for protecting attendant personnel from contamination associated with the use of a medical device which delivers medicinal fluids into a patient, the method comprising the steps of:
  (a) providing the device, the device including a hollow tubular apparatus and a flexible sheath disposed around the apparatus, the apparatus having a body contact end and a non-body contact end, the flexible sheath having an extended position and a stowed-retracted position, the flexible sheath being disposed medial of the body contact end and the non-body contact end, the apparatus having a tip disposed at the body contact end;
  (b) inserting the body contact end of the hollow tubular apparatus into the patient, the flexible sheath being in the stowed-retracted position;
  (c) delivering the medicinal fluids into the patient through the hollow tubular apparatus, the flexible sheath being maintained in the stowed-retracted position,
  (d) removing the body contact end of the hollow tubular apparatus from the patient after the medicinal fluids have been delivered into the patient, the flexible sheath being still maintained in the stowed-retracted position;
  (e) extending the flexible sheath about the body contact end of the hollow tubular apparatus after the apparatus has been removed from the patient, the length of the flexible sheath being great enough to enable the flexible sheath to extend beyond the tip of the apparatus.

5. A method for protecting attendant personnel from contamination associated with the use of a medical device which withdraws body fluids from a patient, the method comprising the steps of:
  (a) providing the device, the device including a hollow tubular apparatus and a flexible sheath disposed around the apparatus, the apparatus having a body contact end and a non-body contact end, retracted position, the flexible sheath being disposed medial of the body contact end and the non-body contact end, the apparatus having a tip disposed at the body contact end;
  (b) inserting the body contact end of the hollow tubular apparatus into the patient, the flexible sheath being maintained in the stowed-retracted position;
  (c) withdrawing the body fluids from the patient through the hollow tubular apparatus, the flexible sheath being maintained in the stowed-retracted position;
  (d) removing the body contact end of the hollow tubular apparatus from the patient after the body fluids have been withdrawnn from the patient, the flexible sheath being still maintained in the stowed-retracted position;
  (e) extending the flexible sheath about the body contact end of the hollow tubular apparatus after the apparatus has been removed from the patient, the length of the flexible sheath being great enough to enable the flexible sheath to extend beyond the tip of the apparatus.

6. A disposable medical device for use in a patient, the device protecting attendant personnel from contamination associated with the device after the device has been withdrawn from the patient, the device comprising:
  (a) a syringe having a body contact end and a non-body contact end, the syringe having a passageway that enables fluids to be transmitted therethrough from and to the circulatory system of the patient, the syringe having a rigid tip disposed at the body contact end; and (b) a flexible sheath being secured to the syringe between the body contact end and the non-body contact end, the flexible sheath having an enveloping position and a stowed-retracted position, the flexible sheath being compactly stowed when in the stowed-retracted position, the flexible sheath being unstowed and extended in the enveloping position, the length of the flexible sheath in the enveloping position being great enough to extend beyond the rigid tip of the syringe; and wherein the flexible sheath is in the stowed-retracted position until after the syringe is removed from the circulatory system of the patient, at which time the flexible sheath is extended beyond the rigid tip of the syringe.

7. A disposabe medical device for use in a patient, the device protecting attendant personnel from contamination associated with the device after the device has been withdrawn from the patient, the device comprising:

(a) a syringe having a body contact end and a non-body contact end, the syringe having a rigid and hollow cannula disposed at the body-contact end, the cannula enabling fluids to be transmitted therethrough from and to the circulatory system of the patient, the cannula having a rigid tip disposed at the body contact end; and (b) flexible means for containing the syringe, the flexible means being secured to the syringe between the body contact enveloping position and a stowed-retracted position, the flexible means being compactly stowed when in the stowed-retracted position, the flexible means being unstowed and extended in the enveloping position, the flexible means being in the stowed-retracted position when the syringe is in the body of the patient, the length of the flexible means in the enveloping position being great enough to extend beyond the tip of the cannula, the flexible means being in the enveloping position when the rigid tip of the syringe is withdrawn from the circulatory system of the patient.

8. A disposable medical device for use in a patient, the device protecting attendant personnel from contamination associated with the device after the device has been withdrawn from the patient, the device comprising:

(a) a syringe having a body contact end and a non-body contact end, the syringe having a hollow cannula disposed at the body-contact end, the cannula enabling fluids to the transmitted therethrough from and to the circulatory system of the patient, the cannula having a rigid tip disposed at the body contact end; and (b) a flexible sheath secured to the syringe between the body contact end and the non-body contact end, the flexible sheath being made of a material that is resistant to tearing and puncture, the flexible sheath having an envelopimng position and a stowed-retracted position, the flexible sheath being compactly stowed when in the stowed-retracted position, the flexible sheath being unstowed and extended in the enveloping position, the flexible sheath being in the stowed-retracted position when the syringe is in the body of the patient, the flexible sheath being in the enveloping position when the cannula has been removed from the circulatory system of the patient, the position being great enough to extend beyond the rigid tip of the cannula.

* * * * *